(12) United States Patent
Jensen

(10) Patent No.: US 11,471,031 B2
(45) Date of Patent: Oct. 18, 2022

(54) ARTICULATED TIP PART FOR AN ENDOSCOPE

(71) Applicant: AMBU A/S, Ballerup (DK)

(72) Inventor: Thomas Bachgaard Jensen, Copenhagen V (DK)

(73) Assignee: AMBU A/S, Ballerup (DK)

(*) Notice: Subject to any disclaimer, the term of this patent is extended or adjusted under 35 U.S.C. 154(b) by 364 days.

(21) Appl. No.: 16/584,517

(22) Filed: Sep. 26, 2019

(65) Prior Publication Data

US 2020/0100648 A1 Apr. 2, 2020

(30) Foreign Application Priority Data

Sep. 28, 2018 (EP) .................................... 18197466

(51) Int. Cl.
| | | |
|---|---|---|
| *A61B 1/008* | (2006.01) | |
| *A61B 1/005* | (2006.01) | |
| *A61B 1/01* | (2006.01) | |
| *A61B 1/012* | (2006.01) | |
| *A61B 1/05* | (2006.01) | |
| *A61B 1/00* | (2006.01) | |

(52) U.S. Cl.
CPC ............ *A61B 1/008* (2013.01); *A61B 1/0055* (2013.01); *A61B 1/01* (2013.01); *A61B 1/012* (2013.01); *A61B 1/05* (2013.01); *A61B 1/00114* (2013.01)

(58) Field of Classification Search
CPC ... A61B 1/0011; A61B 1/0051; A61B 1/0055; A61B 1/0056; A61B 1/0057; A61B 1/0008; A61B 1/01; A61M 2025/015
See application file for complete search history.

(56) References Cited

U.S. PATENT DOCUMENTS

| | | |
|---|---|---|
| 4,998,916 A | 3/1991 | Hammerslag et al. |
| 5,325,845 A | 7/1994 | Adair |
| 8,790,250 B2 | 7/2014 | Petersen et al. |

(Continued)

FOREIGN PATENT DOCUMENTS

| | | |
|---|---|---|
| JP | 2004008638 A | 1/2004 |
| JP | 2009279182 A | 12/2009 |

(Continued)

OTHER PUBLICATIONS

Extended Search Report dated Apr. 5, 2019 in corresponding European Application No. 18197466, 6 pg.

*Primary Examiner* — Michael J Carey
*Assistant Examiner* — Stephen Floyd London
(74) *Attorney, Agent, or Firm* — Faegre Drinker Biddle & Reath LLP

(57) ABSTRACT

An articulated tip part for an endoscope having a number of hingedly connected segments including a distal end segment and a second segment, wherein adjacent segments are interconnected by at least one hinge member, whereby the tip part can be bent by means of the hingedly connected segments, wherein the distal end segment comprises a first steering wire guide for accommodating and guiding a steering wire, and wherein the second segment comprises an insertion guide with an entry in an outer circumferential surface of the second segment and an exit aligned with an entry into the first steering wire guide, whereby an end of a steering wire can be guided into the entry of the first steering wire guide via the insertion guide.

19 Claims, 8 Drawing Sheets

(56) References Cited

U.S. PATENT DOCUMENTS

| | | |
|---|---|---|
| 9,220,400 B2 | 12/2015 | Petersen |
| 10,321,804 B2 | 6/2019 | Jacobsen et al. |
| 2002/0193663 A1 | 12/2002 | Matsuura |
| 2003/0040657 A1* | 2/2003 | Yamaya ................. A61B 90/30 600/107 |
| 2008/0242935 A1 | 10/2008 | Inoue |
| 2008/0266441 A1 | 10/2008 | Ichimura |
| 2009/0163917 A1* | 6/2009 | Potter ............... A61M 25/0147 606/41 |
| 2012/0296167 A1 | 11/2012 | Chen et al. |
| 2013/0041223 A1* | 2/2013 | Kato .................... A61B 1/0051 600/121 |
| 2013/0041314 A1* | 2/2013 | Dillon ............... A61M 25/0136 604/95.04 |
| 2013/0090529 A1 | 4/2013 | Boulais |
| 2014/0187894 A1* | 7/2014 | Bui .................... A61B 18/1492 600/373 |
| 2014/0210976 A1 | 7/2014 | Lin |
| 2014/0243592 A1 | 8/2014 | Kato et al. |
| 2016/0051222 A1 | 2/2016 | Imahashi |
| 2017/0266410 A1 | 9/2017 | Farrell et al. |
| 2018/0228346 A1* | 8/2018 | Sekowski ................ A61B 1/05 |
| 2018/0289242 A1* | 10/2018 | Dai ...................... A61B 1/0055 |
| 2019/0167070 A1* | 6/2019 | Ide ........................ A61B 1/008 |
| 2019/0175007 A1 | 6/2019 | Sorensen et al. |
| 2019/0175875 A1* | 6/2019 | Mirzalou .......... A61M 25/0147 |
| 2019/0254504 A1* | 8/2019 | Ide ...................... A61B 1/0057 |
| 2019/0388163 A1* | 12/2019 | Kim ..................... A61B 1/0008 |
| 2020/0016370 A1* | 1/2020 | Sasaki ..................... A61M 1/84 |
| 2020/0046209 A1 | 2/2020 | Fancher |
| 2021/0146096 A1* | 5/2021 | Yamada ............. A61M 25/0026 |

FOREIGN PATENT DOCUMENTS

| | | | |
|---|---|---|---|
| JP | 2010005277 A | | 1/2010 |
| JP | 2011200399 A | | 10/2011 |
| JP | 2015058118 A | | 3/2015 |
| KR | 20160056725 A | | 5/2016 |
| TW | 201825039 A | * | 7/2018 |
| WO | WO 2010/066790 A1 | | 6/2010 |
| WO | WO 2014/106511 A1 | | 7/2014 |
| WO | WO 2016/188543 A1 | | 12/2016 |

* cited by examiner

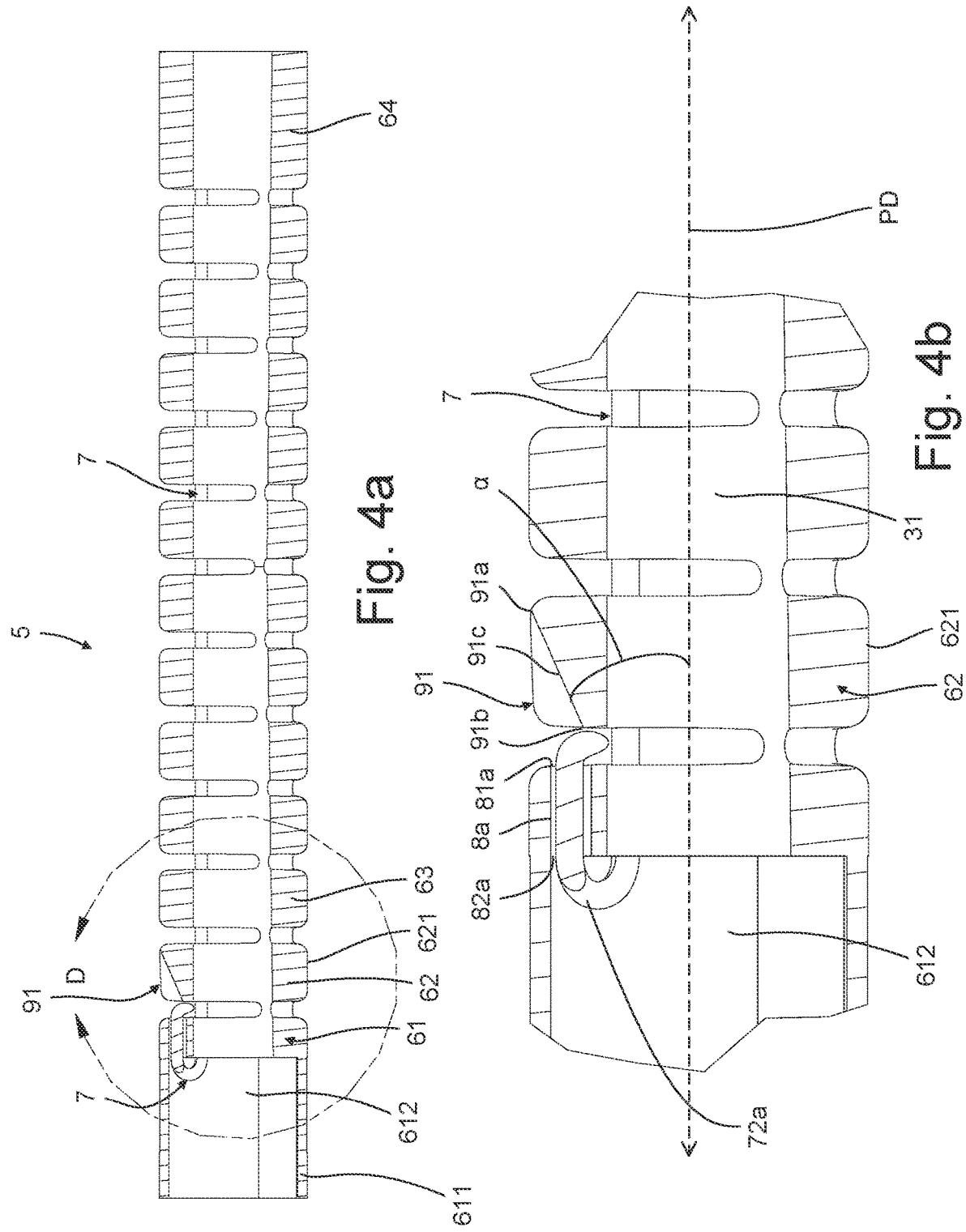

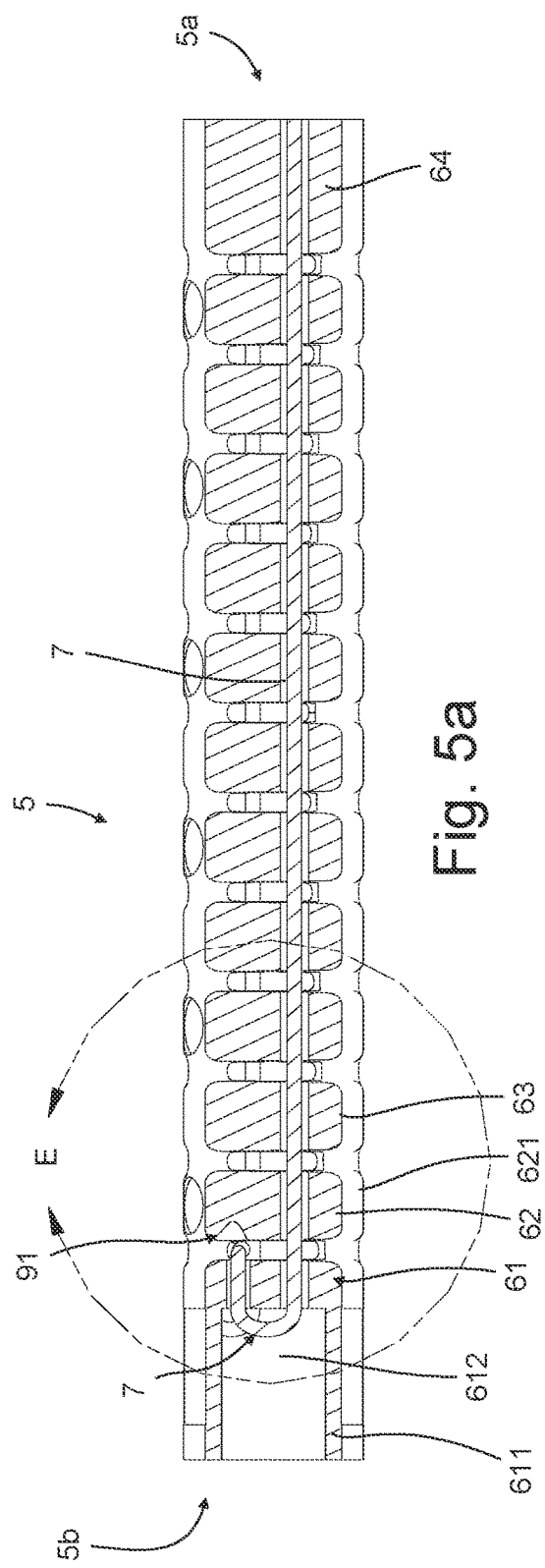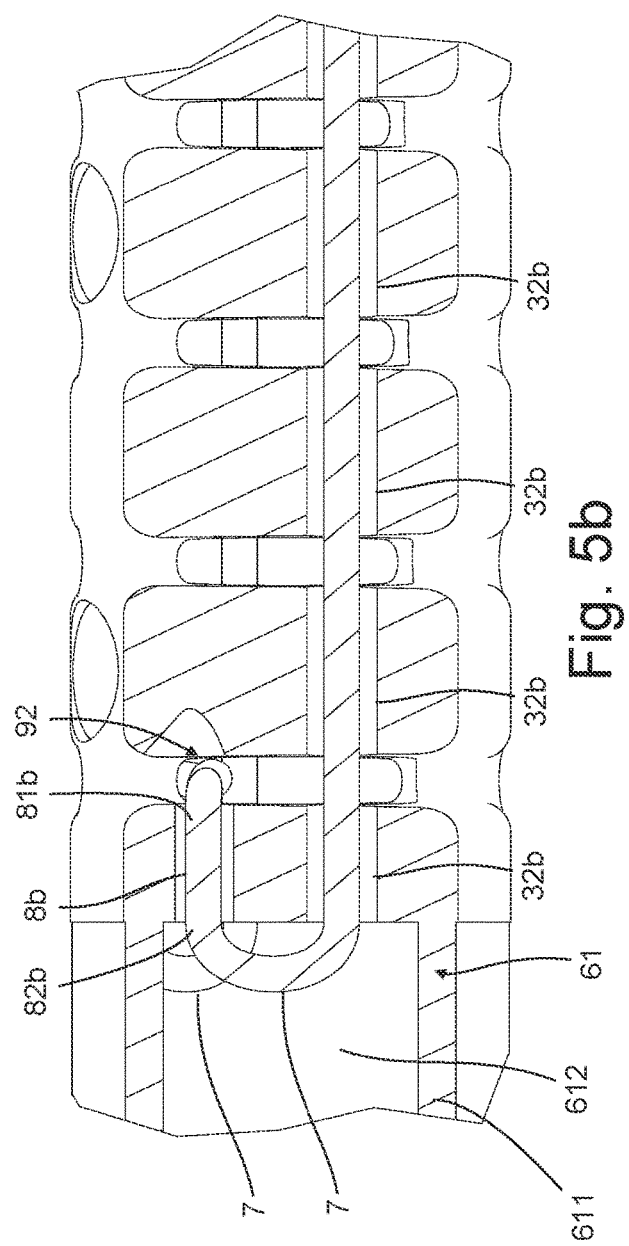

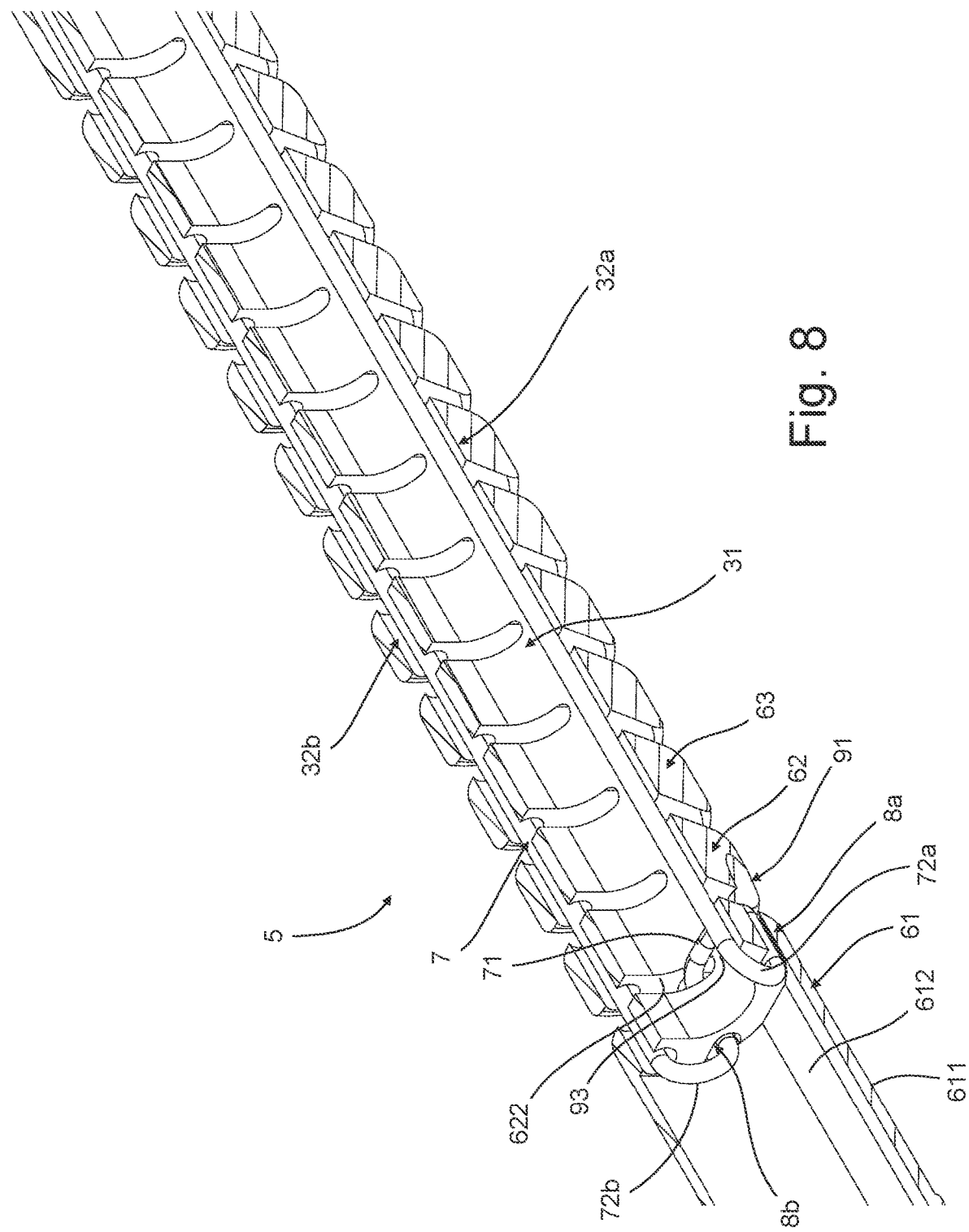

ARTICULATED TIP PART FOR AN ENDOSCOPE

CROSS-REFERENCE TO RELATED APPLICATIONS

This application claims priority from European Patent Application No. 18197466, filed Sep. 28, 2018, which application is incorporated herein by reference thereto.

TECHNICAL FIELD

The present disclosure relates to endoscopes, and more specifically to an articulated tip part for an endoscope.

BACKGROUND

Endoscopes are well known for visually inspecting inaccessible places such as human body cavities. Typically, the endoscope comprises an elongated insertion tube with a handle at the proximal end, as seen from the operator, and visual inspection means, such as a built-in camera, at the distal end of the elongated insertion tube. This definition of the terms distal and proximal, i.e. proximal being the end closest to the operator and distal being the end remote from the operator, as used herein for endoscopes in general, is adhered to in the present specification.

As the name indicates, endoscopes are used for seeing inside things, such as lungs or other human body cavities of a patient. Modern endoscopes are therefore typically equipped with a light source and a vision receptor including a vision sensor, such as a camera or an image sensor. Provided that sufficient light is present, it is possible for the operator to see where the endoscope is steered and to set the target of interest once the tip has been advanced thereto. This therefore normally requires illumination of the area in front of the distal tip of the endoscope, in particular the field of vision of the camera(s). The light source, such as a light emitting diode or an optical fibre, may provide illumination.

Electrical wiring for the camera and other electronics, such as LED lighting accommodated in the tip part at the distal end, run along the inside of the elongated insertion tube from the handle to the tip part. Instead of using cameras, endoscopes may also be fibre-optic, in which case the optical fibres run along the inside of the elongated insertion tube to the tip part. For some applications, a working or suction channel may run along the inside of the insertion tube from the handle to the tip part, e.g. allowing liquid to be removed from the body cavity or allowing for insertion of surgical instruments or the like, into the body cavity. The suction channel may be connected to a suction connector, typically positioned at a handle at the proximal end of the insertion tube. For other applications, the working or suction channel may be omitted.

In order to be able to manoeuvre the endoscope inside the body cavity, the distal end of the endoscope may comprise a bending section with increased flexibility, e.g. an articulated tip part allowing the operator to bend this section. Typically this is done by tensioning or slacking steering wires also running along the inside of the elongated insertion tube from the articulated tip part to a control mechanism of the handle.

An example of such an endoscope is disclosed in international patent application, WO 2014/106511 A1. This endoscope includes a bending section and a steering wire. The steering wire is secured to the distal end of the tip part so that once the steering wire is tensioned, the bending section of the tip part will bend towards the steering wire. This allows manoeuvering the endoscope inside the body cavity.

The steering wire of the prior art are usually secured in the distal end of the tip part by means of threading. One drawback is that threading requires a considerable amount of assembler dexterity which increases the assembly time, an important cost driver especially for single-use endoscopes.

A general desire in the field is to miniaturise the insertion tube of the endoscope, and thus the tip part, as this opens up new fields of application, for instance endoscopes for Ear, Nose, and Throat (ENT) endoscopy, such as rhinoscopy or rhinolaryngoscopy, which requires an insertion tube with a smaller footprint than for instance bronchoscopy. However, the drawbacks of threading are exacerbated when the endoscope is made smaller, since the bending section will be so small that threading passages may be difficult to see for an ordinary assembler.

SUMMARY

On this background, it may be seen as an object of the present disclosure to provide an improved articulated tip part for an endoscope.

One or more of these objects may be met by the disclosed embodiments as described in the following.

An articulated tip part for an endoscope, an endoscope including the articulated tip part, and a method of assembling the articulated tip part and the endoscope are provided.

A first aspect of the disclosure relates to an articulated tip part for an endoscope (hereafter the articulated tip part may also be referred to as the "tip part"), the articulated tip part comprising:

a number of hingedly connected segments including a distal end segment and a second segment, wherein adjacent segments are interconnected by at least one hinge member, whereby the tip part can be bent by means of the hingedly connected segments;

wherein the distal end segment comprises a first steering wire guide for accommodating and guiding a steering wire; and wherein the second segment comprises an insertion guide with an entry in an outer circumferential surface of the second segment and an exit aligned with an entry into the first steering wire guide, whereby an end of a steering wire can be guided into the entry of the first steering wire guide via the insertion guide.

An advantage of a tip part according to embodiments of the disclosure may be that threading one or more steering wires in the number of hingedly connected segments is made easier for the assembler of the tip part, since it has been experienced that positioning the end of a steering wire in an insertion guide is considerably easier than inserting the end in a hole of the distal end segment.

An advantage of a tip part according to embodiments of the disclosure may be that the provision of an insertion guide facilitates assembly of a steering wire by providing a visual indication for the method of assembly.

An advantage of a tip part according to the embodiments of the disclosure may be that the provision of an insertion guide reduces the dexterity required by the assembler.

An advantage of a tip part according to the embodiments of the disclosure may be that the tip part and/or the insertion tube can be made with a smaller footprint, e.g. a smaller diameter. The articulated tip part may be made with a diameter of 3 mm or less. Prior art tubes are typically made with a diameter of 4 mm or greater. A smaller tip part may also allow using the tip part for other applications such as ear, nose, and throat endoscopy, e.g. rhinoscopy and/or rhinolaryngoscopy.

The tip part may extend along a proximal-distal axis. The proximal-distal axis may coincide with a centre line of the tip part. The proximal-distal axis is not necessarily always straight, since the tip part may bend, the proximal-distal axis may still coincide with the centre line of the tip part.

The first and/or second steering wire guide may be provided as a first and/or second steering wire through hole, respectively.

The insertion guide may be a first insertion guide. The distal end segment may comprise a second steering wire guide for accommodating and guiding a steering wire. The second segment may comprise a second insertion guide with an entry in the outer circumferential surface of the second segment and an exit aligned with an entry into the second steering wire guide, whereby an end of a steering wire can be guided into the entry of the second steering wire guide via the second insertion guide.

The second segment may be adjacent to the distal end segment. However, while advantageous, this is not strictly necessary as there could be one or more intermediate segments between the second segment and the distal end segment, and through holes in these intermediate segments may allow direct alignment between the exit of the insertion guide and the entry of the first steering wire guide of the distal end segment.

The second segment and the distal end segment may be interconnected by at least one hinge member. Additionally or alternatively, each pair of adjacent segments may be interconnected by at least one hinge member. Hinge member(s) may be bridging a gap between adjacent segments.

Each segment may comprise a proximal surface facing a distal surface of an adjacent segment forming a gap therein between, and at least one hinge member may bridge the gap. Each segment may comprise a distal surface facing a proximal surface of an adjacent segment forming a gap therein between, and at least one hinge member may bridge the gap. The proximal surface and/or distal surface of each segment may be substantially planar. The exit of the first and/or the second insertion guide may be provided in the distal surface of the second segment.

Each segment may be provided with a similar, potentially equal, circumference. The segments may be substantially disc-shaped. Each segment may be substantially cylindrical disc-shaped with an outer circumferential surface, so that the tip part has a uniform outer contour. The outer circumferential surface may extend around a proximal-distal axis of the tip part.

In this specification, the term "outer surface" may be understood as a surface intended to face, though not necessarily be exposed to, a body cavity when the articulated tip part is inserted into a body. A sleeve or an external sheath may be provided over the outer surface of the tip part and/or the main tube. The sleeve may provide the tip part and/or the main tube with an outer surface which is suitable for exposure to body tissue.

The insertion guide and through hole may be arranged so that a gap is provided between the exit of the insertion guide and the entry of the first steering wire guide.

The number of hingedly connected segments may form part of a bending section of the articulated tip part.

The tip part may comprise one or more light sources positioned at a distal end of the tip part so that light emitted from the light source is directed distally. The light source(s) may be light emitting diode(s) and/or light fibre(s).

The control element may be configured to allow an operator to control the tip part by the at least one steering wire. The control element may allow bending the tip part in at least one direction, potentially in two directions, the two directions potentially being opposite. The control element may be accommodated in an operating handle. The control element may include a lever allowing an operator to control the control element. The lever may extend outwardly from the control element, potentially through the operating handle. The control element may be in the form of a roller or a roller disc.

The operating handle may be suitable for allowing an operator to grip and to operate the endoscope, potentially with one hand. The operating handle may comprise a handle housing arranged at a proximal end of the insertion tube. The handle housing may accommodate the control element.

The tip part may form part of an insertion tube. The tip part may be positioned at a distal end of the insertion tube. The insertion tube may be suitable for insertion into a body cavity, potentially a lung, through a body opening, potentially a mouth, nose, and/or ear. The body may be a natural and/or artificial body, potentially a human body. The insertion tube may extend from the operating handle towards a distal end of the endoscope. The insertion tube may comprise a main tube connected to a proximal end of the tip part.

A sleeve or an external sheath may enclose the tip part and/or the main tube. The sleeve or external sheath may seal the connection between the tip part and the main tube. The sleeve or external sheath may provide the tip part and/or the main tube with an outer surface which is suitable for insertion into a body cavity, e.g. a smooth outer surface.

The tip part may comprise a camera assembly positioned at a distal end of the tip part and allowing an operator to inspect a body cavity, when the tip part is inserted into the body cavity. The camera assembly may comprise one or more selected from the group consisting of: an image sensor configured to capture an image, at least one lens configured to alter light received by the image sensor, a camera housing for supporting the parts of the camera assembly, at least one light source configured to provide illumination for the image sensor, a printed circuit board, at least one signal cable for carrying an image signal from the camera assembly to the operator, and a power cable for supplying the camera assembly with electricity. The printed circuit board may be configured to process a signal from the image sensor. The signal cable and/or the power cable may be connected to printed circuit board. The power cable may be configured to supply power to the printed circuit board.

The segments may comprise at least one cable passage for accommodating at least one cable, e.g. a signal cable for carrying an image signal and/or a power cable for carrying electricity. The cable passage may comprise a through hole in each of the segments, potentially so as to form a cable passage extending from the distal end segment through the intermediate segment(s) to the proximal end segment. The cable passage may be positioned in a centre of the segments. The tip part may comprise a signal cable for carrying an image signal and/or a power cable for carrying electricity positioned in the cable passage.

The tip part may comprise a working passage. The working passage may be configured for accommodating a tube providing a working channel. The working channel may be a suction channel for providing a suction at the distal end of the tip part. The suction channel may be connected to a suction connector, potentially at a handle at the proximal end of the insertion tube. The working channel may allow insertion of surgical instruments there through to the distal end of the tip part. The working passage may be omitted to minimize the size of the tip part.

Additionally or alternatively, the distal end segment may have a circumferential wall enclosing a spacing, and wherein the first steering wire guide may have a exit leading to the spacing of the distal end segment.

Additionally or alternatively, the insertion guide may form a duct.

This may provide the advantage that threading the wire is further facilitated.

Additionally or alternatively, the insertion guide may form a recess, a trough, a hole, a notch, and/or a slit. The insertion guide may be formed by a hole through the second segment with an entry opening in the outer circumferential surface and an exit aligned with the entry of the steering wire guide.

Additionally or alternatively, the insertion guide, potentially a bottom of the insertion guide, may form a ramp.

This may provide the advantage that the end of the steering wire may increasingly be predisposed for extending into the steering wire guide, since the ramp can be adjusted to correspond to the predominant insertion angle of the assembler.

The ramp may taper off towards a distal end of the tip part. The ramp may taper off from the entry of the insertion guide to the exit of the insertion guide. The entry of the insertion guide may be arranged flush with the outer circumferential surface of the second segment. The entry and exit of the insertion guide may be arranged along the proximal-distal axis. The ramp, or the bottom of the insertion guide may form an angle in relation to the proximal-distal axis, potentially in relation to a centre line of the second segment. The angle may potentially be in the range of 15°-45°, in the range of 20°-40°, or preferably about 30°. This has been found to potentially improve the success rate of threading the steering wire into the steering wire guide.

Additionally or alternatively, the at least one hinge member may be a film hinge and/or an integral hinge and/or a living hinge.

This may provide the advantage, that these hinge types are easy to form simultaneously with forming the insertion guide. This may especially be the case if the tip part is moulded in one piece.

The at least one hinge member may alternatively be any other suitable hinge type.

Additionally or alternatively, the number of hingedly connected segments may comprise a steering wire passage, potentially having a through hole in the distal end segment and/or in each of the number of hingedly connected segments.

The steering wire passage may be configured to enclose or surround a steering wire positioned therein.

The steering wire passage may be substantially straight, potentially when the tip part is in an unbent or resting position. The trough holes of the steering wire passage may be positioned to enclose a straight line, potentially when the tip part is in an unbent or resting position.

The steering wire passage may be a first steering wire passage and the number of hingedly connected segments may comprise a second steering wire passage, potentially having a through hole in the distal end segment or in each of the number of hingedly connected segments. The second steering wire passage may be provided similarly to the first steering wire passage. The through holes of the second steering wire passage may be different from the through holes of the first steering wire passage. The first steering wire passage and the second steering wire passage may be symmetrically positioned, potentially on opposite sides of the number of hingedly connected segments.

Additionally or alternatively, the number of hingedly connected segments may comprise a plurality of intermediate segments, wherein the plurality of intermediate segments may include the second segment, and wherein adjacent segments may be interconnected by at least one hinge member.

Additionally or alternatively, the number of hingedly connected segments may comprise a proximal end segment configured for connection with the remaining parts of the endoscope, potentially a main tube of the endoscope.

Additionally or alternatively, the distal end segment, the at least one hinge member, and the second segment may be integrally formed in one piece. The number of hingedly connected segments or the bending section may be integrally formed in one piece.

Additionally or alternatively, the outer circumferential surface of each hingedly connected segment may be substantially cylindrically shaped, so that the tip part may have a uniform outer contour.

The outer circumferential surface of each segment may extend around the proximal-distal axis of the tip part.

Additionally or alternatively, the articulated tip part may comprise a steering wire positioned in the insertion guide and in the steering wire guide.

The steering wire may further be positioned in the steering wire passage. The steering wire may be secured to the distal end of the tip part, potentially to the distal end segment, by means of a friction engagement. At least one end, potentially two ends, of the steering wire may be connected to the control handle, potentially to the control lever of the control handle, whereby the movement of the control handle causes the articulated tip part to bend.

The tip part may comprise a steering wire positioned in the insertion guide and in the steering wire guide. The steering wire may further be positioned in a steering wire passage. An end of the steering wire may be secured in the distal end of the tip part, and another end of the steering wire may be connected to a control element, potentially connected to a control lever of control handle. Thus by manipulating the control element the steering wire may be tensioned on one side of the plane of the hinge members, and slacked on the other, thus allowing the bending section to bend in a desired direction.

The steering wire may be a first steering wire and the articulated tip part may further comprise a second steering wire, potentially provided similarly to the first steering wire. The second steering wire may be positioned in the second steering wire passage.

Additionally or alternatively, a section, potentially an intermediate or middle section, of the steering wire may be secured at the distal end of the tip part by means of a friction engagement.

A friction engagement may be a particularly simple way of securing the steering wire.

The friction engagement may be formed by at least one, potentially at least two, or potentially three, bend(s) of the steering wire. The bend(s) may be provided at the distal end segment.

Additionally or alternatively, the tip part may form part of an endoscope and may be positioned at a distal end of the endoscope.

Additionally or alternatively, the endoscope may form part of a system for visually inspecting inaccessible places such as human body cavities, the system further comprising a monitor. The endoscope may be connectable to the monitor, and the monitor may allow an operator to view an image captured by the camera assembly of the endoscope.

A second aspect of the disclosure relates to a use of an articulated tip part according to the first aspect of the disclosure. The articulated tip part may be used as a part of an endoscope, potentially for Ear, Nose, and Throat (ENT) endoscopy, such as rhinoscopy or rhinolaryngoscopy.

A third aspect of the disclosure relates a method for guiding a steering wire in an articulated tip part for an endoscope according to the first aspect of the disclosure, the method may comprise a step of guiding an end of a steering wire into the entry of the first steering wire guide via the insertion guide.

An advantage of a method according to the embodiments of the disclosure may be that threading one or more steering wires in the number of hingedly connected segments is made easier for the assembler of the tip part.

An advantage of a method according to the embodiments of the disclosure may be that the provision of an insertion guide facilitates assembly of a steering wire by providing a visual indication for the method of assembly.

The method may comprise a step, potentially performed prior to the step of guiding an end of a steering wire into the entry of the first steering wire guide via the insertion guide, of inserting an end of the steering wire between two adjacent segments of the tip part. At least one of the adjacent segments may comprise the insertion guide. The two adjacent segments may be the distal end segment and the second segment. The end of the steering wire may potentially be inserted in a gap between two hinge member connecting the two adjacent segments.

The method may comprise a step of guiding another end of the steering wire into the entry of the second steering wire guide via a second, different insertion guide. The steering wire may thus form an intermediate bend from the first steering wire guide to the second steering wire guide.

The method may comprise a step of guiding the first and/or the second end of the steering wire through a respective first and/or second steering wire passage.

A person skilled in the art will appreciate that any one or more of the above aspects of the disclosure and embodiments thereof may be combined with any one or more of the other aspects of the disclosure and embodiments thereof.

BRIEF DESCRIPTION OF DRAWINGS

The embodiments summarized above will now be described in greater detail based on non-limiting exemplary embodiments and with reference to the drawings, on which:

FIG. 4a shows a cross-sectional view of the tip part along the line B-B of FIG. 3a;

FIG. 4b shows detail view D of the tip part shown in FIG. 4a;

FIG. 5a shows a cross-sectional view of the tip part along the line C-C of FIG. 3a;

FIG. 5b shows detail view E of the tip part shown in FIG. 5a;

FIG. 8 shows a perspective view of a section of a tip part after being threaded with sections of the tip part omitted for visualisation purposes.

DETAILED DESCRIPTION

Figure 1A:
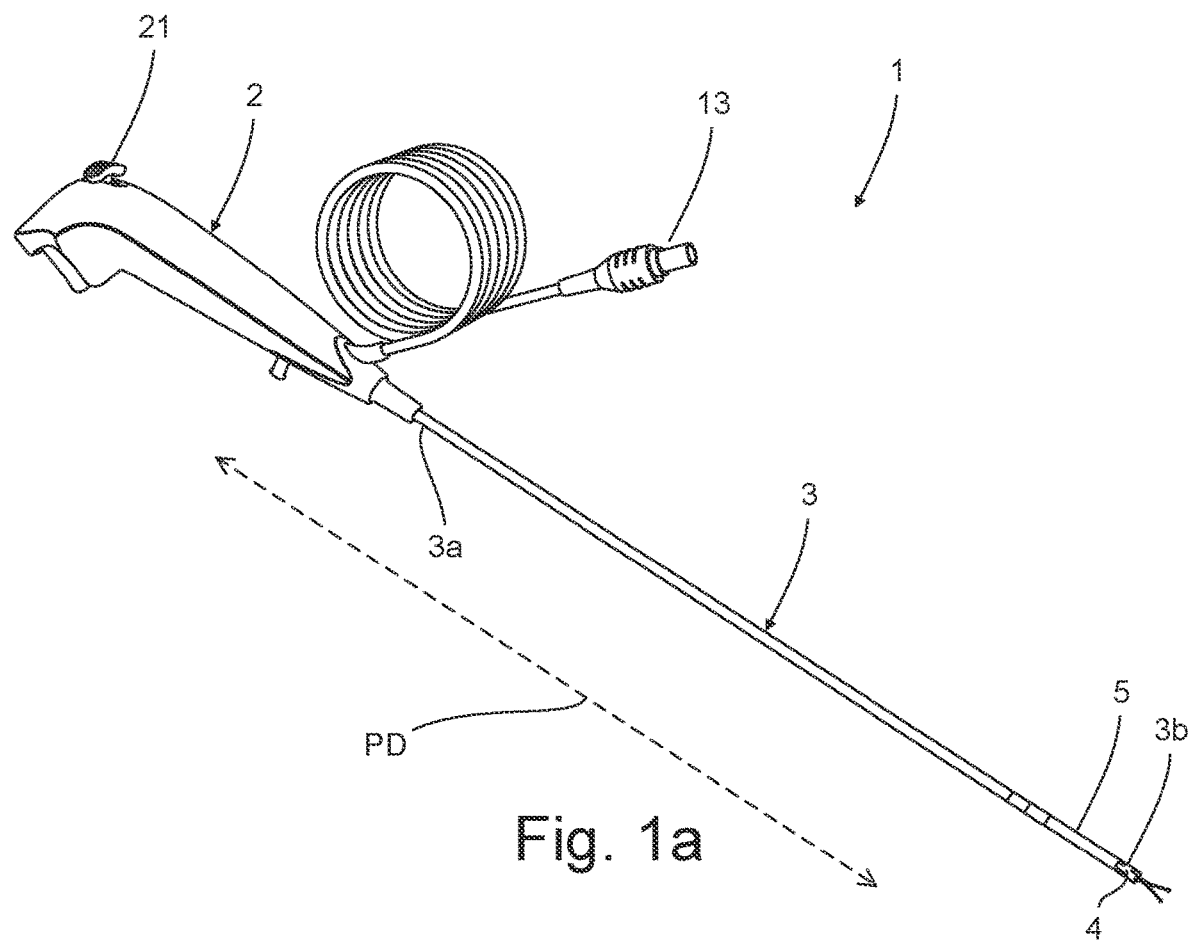
FIG. 1a shows a perspective view of an endoscope in which a tip part according to the present disclosure is implemented.

Referring first to FIG. 1a, an endoscope 1 is shown. The endoscope is disposable, and not intended to be cleaned and reused. The endoscope 1 comprises an elongated insertion tube 3. At the proximal end 3a of the insertion tube 3 an operating handle 2 is arranged. The operating handle 2 has a control lever 21 for maneuvering an articulated tip part 5 at the distal end 3b of the insertion tube 3 by means of a steering wire 7 (visible in FIG. 2a). A camera assembly 4 is positioned in the articulated tip part 5 and is configured to transmit an image signal through a monitor cable 13 of the endoscope 1 to a monitor 11, shown in FIG. 1b. The camera assembly 4 comprises an image sensor, at least a lens distal of the image sensor, and an illumination source, such as a light emitting diode. A view reflected from an object located distally of the camera assembly is captured by the image sensor, where it is digitized and transmitted to the monitor 11.

Figure 1B:
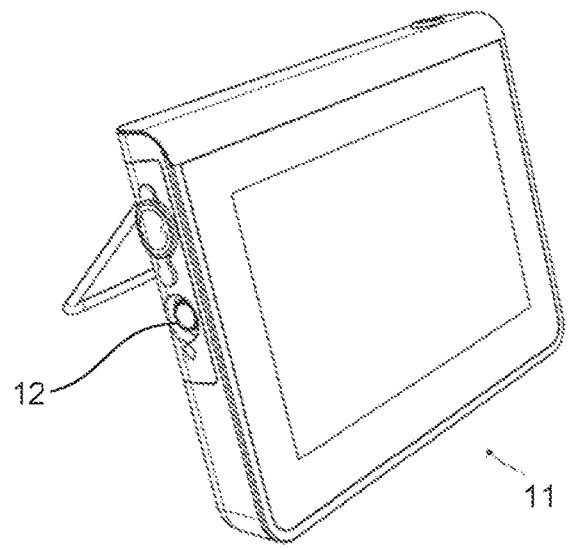
FIG. 1b shows a persepctive view of a monitor to which the endcope of FIG. 1a is connectable.

In FIG. 1b, a monitor 11 is shown. The monitor 11 may allow an operator to view an image based on a view captured by the camera assembly 4 of the endoscope 1. The view may be captured by an image sensor and digitally processed before and/or after it is transmitted via the image signal. The monitor 11 comprises a cable socket 12 to which the monitor cable 13 of the endoscope 1 can be connected to establish a signal communication between the camera assembly 4 of the endoscope 1 and the monitor 11.

Figure 2A:
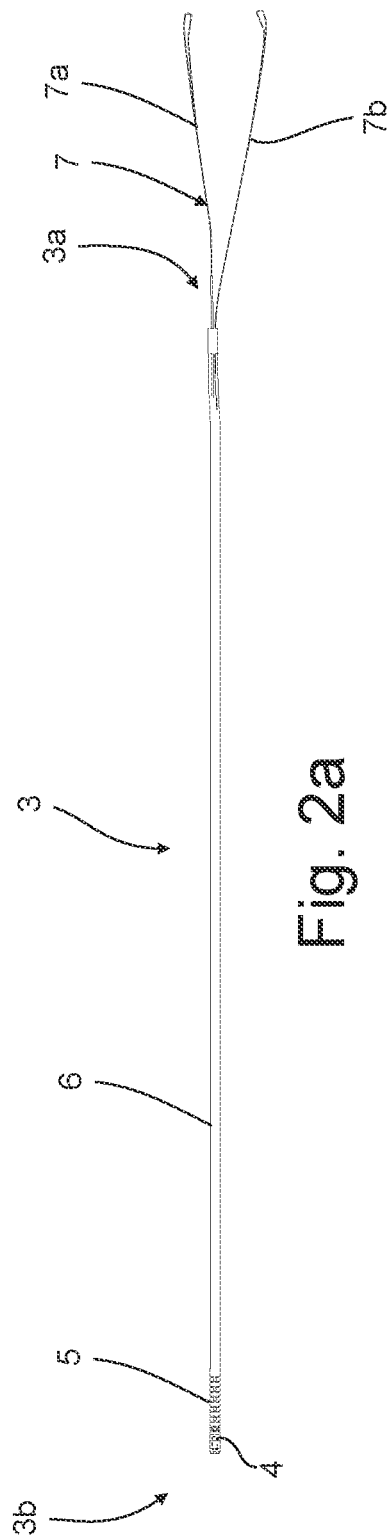
FIG. 2a shows a side view of an insertion tube in which a tip part according to the present disclosure is implemented.

Turning now to FIG. 2a, details of the insertion tube 3 are shown. The insertion tube comprises the articulated tip part 5 positioned at the distal end 3b of the insertion tube 3. A proximal end of the articulated tip part 5 is connected to a main tube 6. Some parts, such as an external sheath or sleeve normally covering and sealing the connection between the articulated tip part 5 and the main tube 6, have been removed for clarity. A steering wire 7 runs inside the main tube 6 and the articulated tip part 5, so that both ends extend from the proximal end 3a of the insertion tube 3. An intermediate section of the steering wire 7 is secured at the distal end of the articulated tip part 5, so that one half of the steering wire 7 runs along one side of the articulated tip part 5 and another half of the steering wire 7 runs along another, opposite side of the articulated tip part 5. The two free ends 7a, 7b of the steering wire 7 are, in the assembled endoscope, connected to a control lever 21 of an operating handle 2. Thus by manipulating the control lever 21 the steering wire 7 may be tensioned on one side of the articulated tip part 5, and slacked on the other, thus allowing the articulated tip part 5 to bend in a desired direction.

Figure 2B:
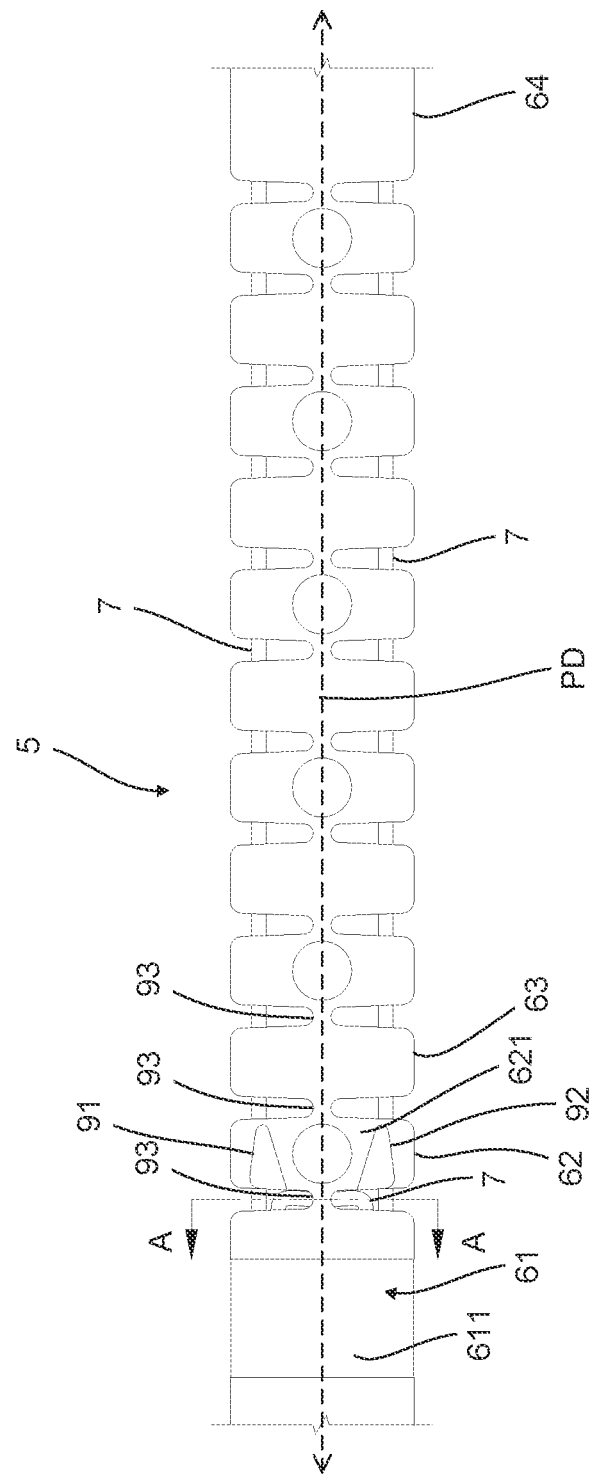
FIG. 2b shows a side view of a section of a tip part according to the present disclosure.

Turning to FIG. 2b, the articulated tip part 5 comprises a number of segments 61, 62, 63, 64. More specifically a distal end segment 61, a proximal end segment 64 for connection to the main tube 6 of the insertion tube 3, and a number of intermediate segments 62, 63. One of the intermediate segments, e.g. intermediate segment 62, may also be referred to as the "second segment". Only the two intermediate segments 62, 63 adjacent to the distal end segment 61 are marked with reference numerals, however the remaining intermediate segments are provided substantially equally. In the illustrated embodiments, the number of intermediate segments 62, 63 is eleven, but the skilled person will understand that the precise number is less important. Each segment is substantially cylindrical disc-shaped with an outer circumferential surface, so that the articulated tip part 5 has a uniform outer contour. A proximal-distal axis PD coincides with a centre line extending through the centre of each segment 61, 62, 63, 64 of the articulated tip part 5. Each intermediate segment comprises a proximal substantially planar surface facing a substantially planar distal surface of an adjacent segment forming a gap therein between, and a substantially planar distal surface facing a substantially planar proximal surface of an adjacent segment forming a gap therein between. As also shown in FIG. 3b, each gap is bridged by two flexible hinge members 93 positioned near the circumference of the articulated tip part 5, so as allow the articulated tip part 5 to bend.

The distal end segment 61, the intermediate segments 62, 63, the proximal end segment 64, and the hinge members 93 interconnecting the segments are integrally formed in one piece.

The second segment 62 comprises two insertion guides 91, 92 each formed as a recess in an outer circumferential surface 621 of the second segment 62.

Figure 3A:
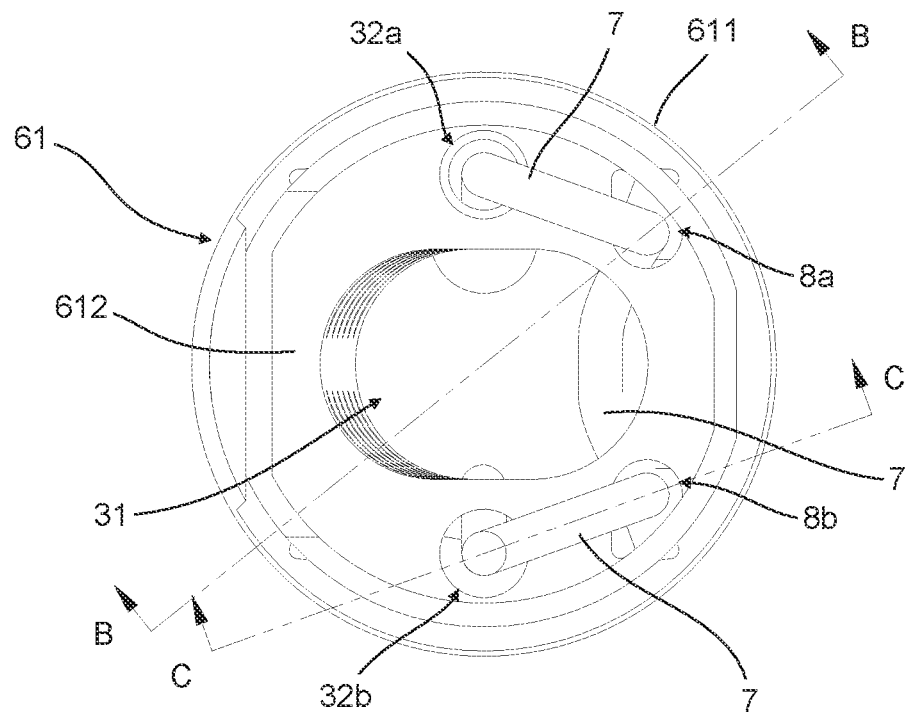
FIG. 3a shows a front view of the tip part in which a camera assembly is omitted.
Figure 3B:
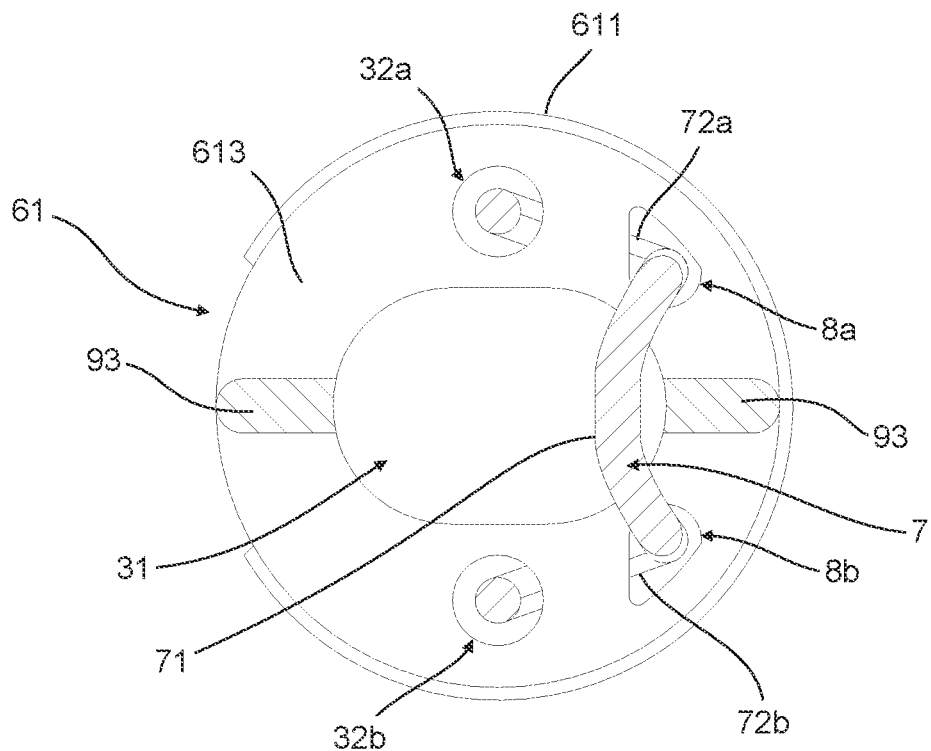
FIG. 3b shows a cross-sectional view of the tip part along the line A-A of FIG. 2b.

Turning now to FIG. 3a, the distal end segment 61 has a circumferential wall 611 enclosing a spacing 612, a proximal wall 615 having a proximal surface 613 spaced apart from a distal surface 614, wherein the proximal wall 615 is disposed proximally of the spacing 612 and adjacent the second segment 62. Normally, the distal end segment 61 comprises a camera assembly with an image sensor and light emitting diodes in the spacing 612, however in these figures the camera assembly has been omitted for clarity. The distal end segment 61 also has a first steering wire guide 8a, and a second steering wire guide 8b, disposed on the proximal wall 615. The steering wire guides 8a, 8b each has an entry 81a, 81b in or adjacent the proximal surface 613 of the distal wall 615 and an exit 82a, 82b in the distal surface 614 of the distal end segment 61, as seen in FIGS. 3b, 4b.

The segments 61, 62, 63, 64 comprise a cable passage 31, a first steering wire passage 32a, and a second steering wire passage 32b. The cable passage 31 can be seen in FIGS. 4a-4b and is for accommodating a signal cable for carrying an image signal from a camera assembly (not shown) incorporated in the distal end segment 61 and a power cable for carrying electricity to the camera assembly. The second steering wire passage 32b can be seen in FIG. 5a-5b, however the first steering wire passage 32a is provided substantially equally. The steering wire passages 32a, 32b are for accommodating the steering wire 7 and for securing that the steering wire 7 in the passages 32a, 32b does not move transversely in relation to the articulated tip part 5. The cable passage 31 and the steering wire passages 32a, 32b are formed by aligned through holes provided in each segment, so as to form three separate, passages 31, 32a, 32b extending from the distal end segment 61 through the intermediate segments 62, 63 to the proximal end segment 64. The passages 31, 32a, 32b are straight when the tip part 5 is in a relaxed state. The cable passage 31 is provided along a centre of each segment, and the steering wire passages 32a, 32b are provided symmetrically on opposite sides of the cable passage 31.

As seen in FIG. 3b, each of the intermediate segments 62, 63 are interconnected with adjacent segments by the means of two flexible hinge members 93 arranged symmetrically on opposite sides in proximity to the circumference of the tip part 5. This type of hinge member may be known as a film hinge, an integral hinge, or a living hinge, however other types of hinges may be suitable.

Turning to FIGS. 4a and 4b showing details of the first insertion guide 91, however the second insertion guide 92 is provided substantially equally to the first insertion guide 91. Each of the insertion guides 91, 92 has an exit 91b aligned with an entry 82a, 82b of the first steering wire guide 8a, 8b. The insertion guides 91, 92 are each provided as a duct with a bottom 91c, forming a ramp which tapers off from the entry 91a, of each insertion guide 91, 92 towards the exit 91b, of each insertion guide 91, 92. Accordingly, a cross-sectional area of the entry 91a of each insertion guide 91, 92 is larger than a cross-sectional area of the respective exit 91b of each insertion guide 91, 92. The entry 91a of each insertion guide 91, 92 are arranged flush with the outer circumferential surface 621 of the second segment 62. The bottom 91c of the first insertion guide 91 forms an angle α with the proximal-distal axis PD of about 30° like the bottom of the second insertion guide 92.

Figure 6:
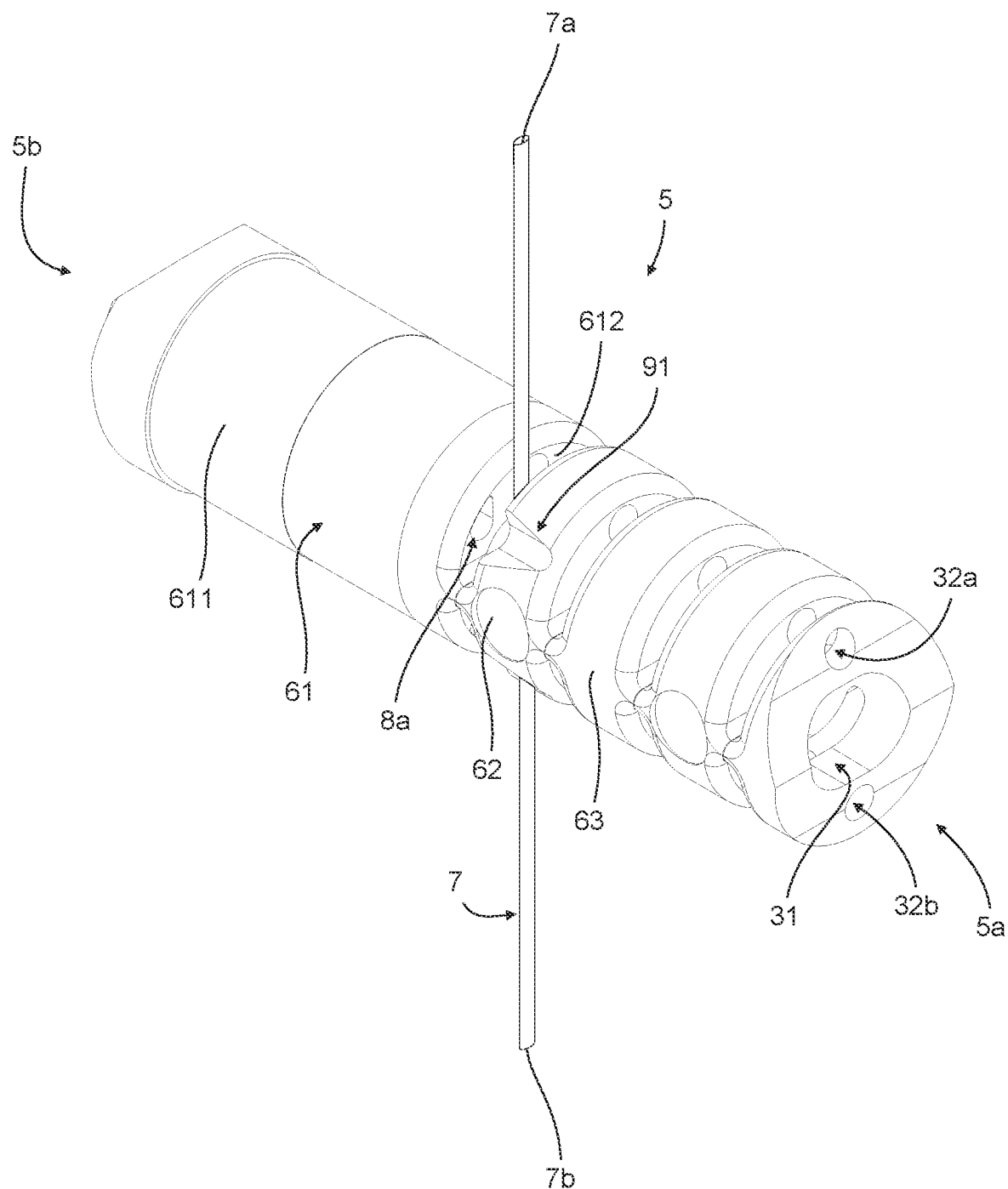
FIG. 6 shows a perspective view of a section of a tip part prior to being threaded.
Figure 7:
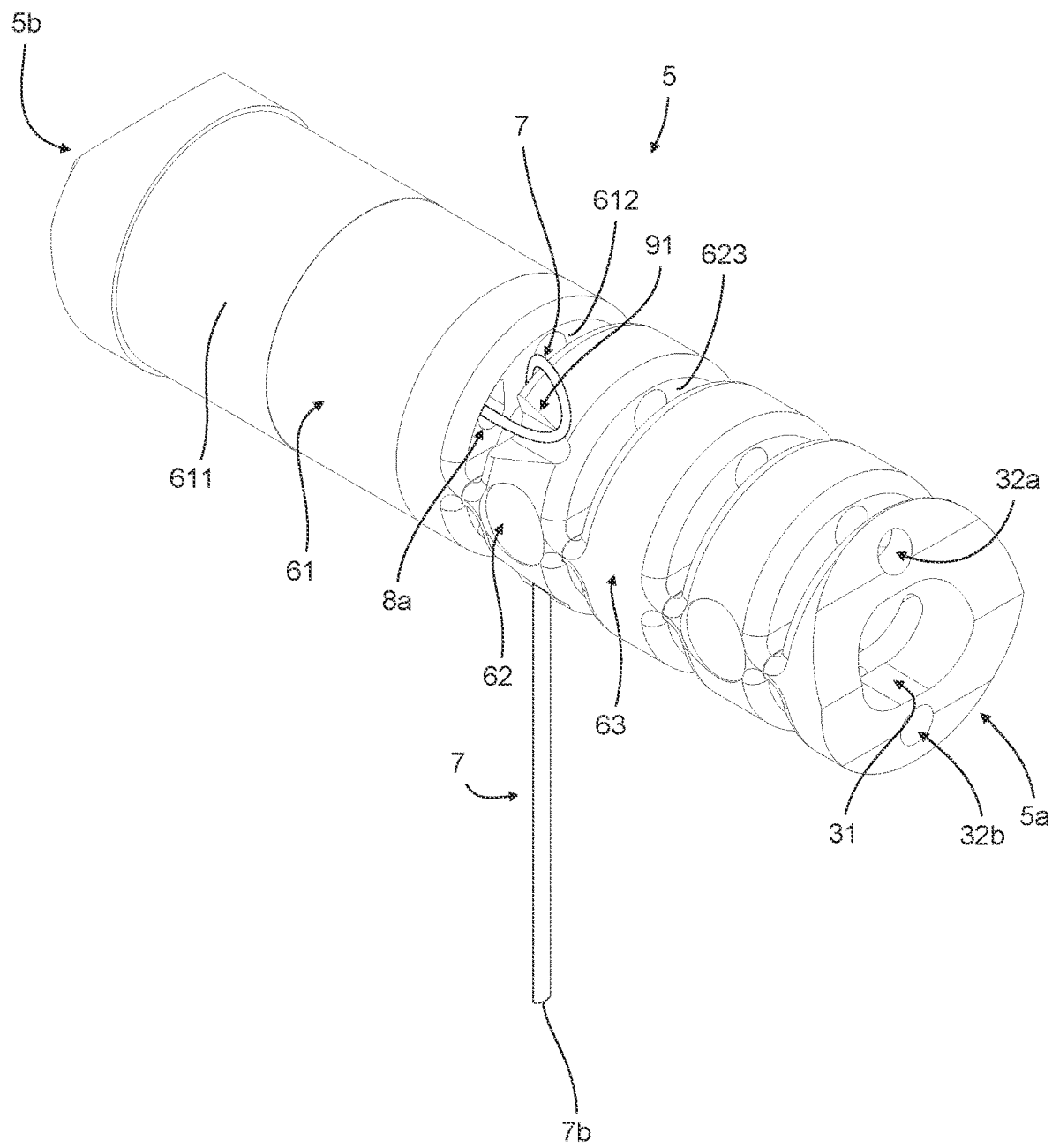
FIG. 7 shows a perspective view of a section of a tip part being partially threaded.

In the following, a method of inserting and securing a steering wire 7 will be described, wherein the steps are performed sequentially. Firstly, the steering wire 7 and an articulated tip part 5 according to the present disclosure are provided. Secondly, as can be seen in FIG. 6, the steering wire 7 is positioned so that it extends through a gap formed by the distal end segment 61, the second segment 62, and the two hinge members 93 interconnecting the distal 61 and second segment 62, and so that a first end 7a of the steering wire 7 extends on one side of the articulated tip part 5, notable above on the figure, and a second end 7b of the steering wire 7 extends on another, different side of the articulated tip part 5, notably below on the figure. Thirdly, the first end 7a of the steering wire is guided by inserting it into the entry 91a of the first insertion guide 91 and sliding the first steering wire end 7a along the bottom 91c of the insertion guide 91, and until the first steering wire end 7a exits the insertion guide 91 through the exit 91b thereof. This ensures that as the steering wire 7 is pushed further, the first steering wire end 7a will enter the entry 81a of the first steering wire guide 8a to arrive at the arrangement shown in FIG. 7. The step is then repeated for second end 7b of the steering wire 7, so that the ends 7a, 7b of the steering wire 7 extend through the respective steering wire guides 8a, 8b, and into the spacing 612 of the distal end segment 61, so that the steering wire 7 forms an intermediate steering wire bend 71 in the gap between the distal end segment 61 and the second segment 62. The steering wire bend 71 is positioned between the hinge members 93 and abutting one of the two hinge members 93. Fourthly, the ends 7a, 7b of the steering wire 7 is lead in a distal to proximate direction through the respective steering wire passages 32a, 32b, so that the ends of the steering wire 7a, 7b extend from the proximal end segment 64 arriving at the arrangement shown in FIG. 8, and so that the steering wire 7 forms a first steering wire bend 72a between the first steering wire guide 8a and the first steering wire passage 32a, and a second steering wire bend 72b between the second steering wire guide 8b and the second steering wire passage 32b. This ensures that the steering wire 7 is secured to the distal end segment 61 of the articulated tip part 5 by a friction engagement, which prevents the steering wire 7 from sliding in the steering wire guides 8a, 8b when an end of the steering wire 7 is pulled.

The tip part 5 can then be attached to the remaining parts of the insertion tube 3 and the endoscope 1.

In another embodiment of a method for inserting a steering wire in a tip part for an endoscope, the method comprises:

providing segments including a distal end segment and a second segment hingedly interconnected by at least one hinge member to enable bending of the tip part, wherein the distal end segment comprises a first steering wire guide and a proximal wall having a proximal surface spaced apart from a distal surface, the first steering wire guide having an entry adjacent the distal surface and an exit disposed on the proximal surface and fluidly connected with the entry, and wherein the second segment comprises a first insertion guide with an entry in an outer circumferential surface of the second segment and an exit aligned with the entry of the first steering wire guide;

aligning a first end of the steering wire with the first insertion guide; and guiding the first end of the steering wire into the entry of the first steering wire guide via the first insertion guide.

In a variation of the present embodiment, thee method further comprising passing the first end of the steering wire through the exit of the first steering wire guide in a distal direction; passing the first end of the steering wire through a first through-hole in the proximal wall, in a proximal direction; aligning the first end of the steering wire with a second insertion guide of the second segment; guiding the first end of the steering wire into an entry of a second steering wire guide in the proximal wall via the second insertion guide; and passing the first end of the steering wire through a second through-hole in the proximal wall, in a proximal direction. In one example of the present variation, the steering wire comprises a second intermediate section and a third intermediate section, the second intermediate section between the first intermediate section and the third intermediate section, and the method further comprises pulling on the steering wire until the third intermediate section is secured to the proximal wall. The method may further comprise securing the first end of the steering wire and the second end of the steering wire to a rotatable actuator located in a handle of the endoscope, the rotatable actuator configured to simultaneously pull and push the first end of the steering wire and the second end of the steering wire, respectively, to articulate the tip part when the rotatable actuator is rotated.

The following is a list of reference numerals used throughout this specification.
1 endoscope
2 handle
21 control lever
3 insertion tube
3a proximal end of insertion tube
3b distal end of insertion tube
4 camera assembly
31 cable passage
32a first steering wire passage
32b second steering wire passage
5 tip part
5a proximal end
5b distal end
6 main tube
61 distal end segment
611 outer circumferential wall
612 spacing
613 proximal surface
614 distal surface
615 proximal wall
62 second segment
621 outer circumferential surface
622 distal surface
623 proximal surface
63 third segment
64 proximal end segment
7 steering wire
7a first end of steering wire
7b second end of steering wire
71 intermediate steering wire bend
72a first steering wire bend
72b second steering wire bend
8a first steering wire guide
81a entry
82a exit
8b second steering wire guide
81b entry
82b exit
91 first insertion guide
91a entry
91b exit
91c bottom
second insertion guide
93 hinge member
PD proximal-distal axis

The invention claimed is:

1. An articulated tip part for an endoscope, the articulated tip part comprising:

segments including a distal end segment and a second segment, wherein the segments are hingedly interconnected by at least one hinge member to enable bending of the tip part, wherein the distal end segment comprises a first steering wire guide for accommodating and guiding a steering wire and a proximal wall having a proximal surface spaced apart from a distal surface, the first steering wire guide having an entry adjacent the proximal surface and an exit disposed on the distal surface and fluidly connected to the entry, and wherein the second segment comprises an insertion guide with an entry in an outer circumferential surface of the second segment, an exit aligned with the entry of the first steering wire guide, and a ramp extending from the entry to the exit and angled relative to a proximal-distal direction to guide an end of the steering wire into the entry of the first steering wire guide.

2. The articulated tip part of claim 1, wherein the distal end segment has a circumferential wall enclosing a spacing, and wherein the exit of the first steering wire guide leads to the spacing of the distal end segment.

3. The articulated tip part of claim 1, wherein the insertion guide forms a duct.

4. The articulated tip part of claim 1, wherein the at least one hinge member is a film hinge and/or an integral hinge and/or a living hinge.

5. The articulated tip part of claim 1, further comprising a first steering wire passage having a first through-hole in the proximal wall of the distal end segment.

6. The articulated tip part of claim 1, wherein the segments comprise a plurality of intermediate segments which includes the second segment, and wherein the plurality of intermediate segments are interconnected by at least one hinge member.

7. The articulated tip part of claim 6, wherein the plurality of intermediate segments comprises a proximal end segment configured for connection with remaining parts of the endoscope.

8. The articulated tip part of claim 1, wherein the distal end segment, the at least one hinge member, and the second segment are integrally formed in one piece.

9. The articulated tip part of claim 1, wherein the articulated tip part has an outer circumferential surface that is substantially cylindrically shaped, so that the articulated tip part has a uniform outer contour.

10. The articulated tip part of claim 1, wherein the distal end segment comprises a circumferential wall extending from the proximal wall and defining a spacing, wherein the articulated tip part further comprises a first through-hole in the proximal wall of the distal end segment, and a steering wire having a first end, a first intermediate section, and a second end opposite the first end with the first intermediate section therebetween, wherein whence assembled the steering wire passes through the first steering wire guide and the first through-hole with the first intermediate section positioned in the spacing.

11. The articulated tip part of claim 10, further comprising a second steering wire guide and a second through-hole, wherein the steering wire has a second intermediate section and a third intermediate section, the second intermediate section between the first intermediate section and the third intermediate section, wherein the steering wire passes through the second steering wire guide and the second through-hole with the third intermediate section positioned in the spacing and the second intermediate section positioned proximally of the proximal surface of the proximal wall to secure the steering wire by friction engagement with the proximal wall.

12. An endoscope comprising a tip part according to claim 10, the tip part being positioned at a distal end of the endoscope and comprising a camera assembly at least partly disposed in the spacing.

13. A system for visually inspecting human body cavities, the system comprising:
   an endoscope according to claim 12; and
   a monitor,
   wherein the endoscope is connectable to the monitor to present an image of a view captured by the camera assembly of the endoscope.

14. A method for inserting a steering wire in a tip part for an endoscope, the method comprising:
   providing segments including a distal end segment and a second segment hingedly interconnected by at least one hinge member to enable bending of the tip part, wherein the distal end segment comprises a first steering wire guide and a proximal wall having a proximal surface spaced apart from a distal surface, the first steering wire guide having an entry adjacent the proximal surface and an exit disposed on the distal surface and fluidly connected with the entry, and wherein the second segment comprises a first insertion guide with an entry in an outer circumferential surface of the second segment, an exit aligned with the entry of the first steering wire guide, and a ramp extending from the entry to the exit and angled relative to a proximal-distal direction to guide a first end of the steering wire into the entry of the first steering wire guide;
   aligning the first end of the steering wire with the first insertion guide; and
   guiding the first end of the steering wire into the entry of the first steering wire guide via the first insertion guide.

15. The method of claim 14, further comprising:
   passing the first end of the steering wire through the exit of the first steering wire guide in a distal direction;
   passing the first end of the steering wire through a first through-hole in the proximal wall, in a proximal direction;
   aligning the first end of the steering wire with a second insertion guide of the second segment;
   guiding the first end of the steering wire into an entry of a second steering wire guide in the proximal wall via the second insertion guide; and
   passing the first end of the steering wire through a second through-hole in the proximal wall, in a proximal direction.

16. The method of claim 15, wherein the steering wire comprises a first intermediate section, a second end, a second intermediate section and a third intermediate section, the second intermediate section between the first intermediate section and the third intermediate section, the method further comprising:
   pulling on the steering wire until the third intermediate section is secured to the proximal wall.

17. The method of claim 16, further comprising:
   securing the first end of the steering wire and the second end of the steering wire to a rotatable actuator located in a handle of the endoscope, the rotatable actuator configured to simultaneously pull and push the first end of the steering wire and the second end of the steering wire, respectively, to articulate the tip part when the rotatable actuator is rotated.

18. The articulated tip part of claim 1, wherein the first insertion guide has an entry cross-sectional area and an exit cross-sectional area that is smaller than the entry cross-sectional area.

19. The articulated tip part of claim 18, wherein when viewed longitudinally the exit of the first insertion guide traverses the entry of the first steering wire guide.

* * * * *